MAPLE TREE
Filed Dec. 5, 1967
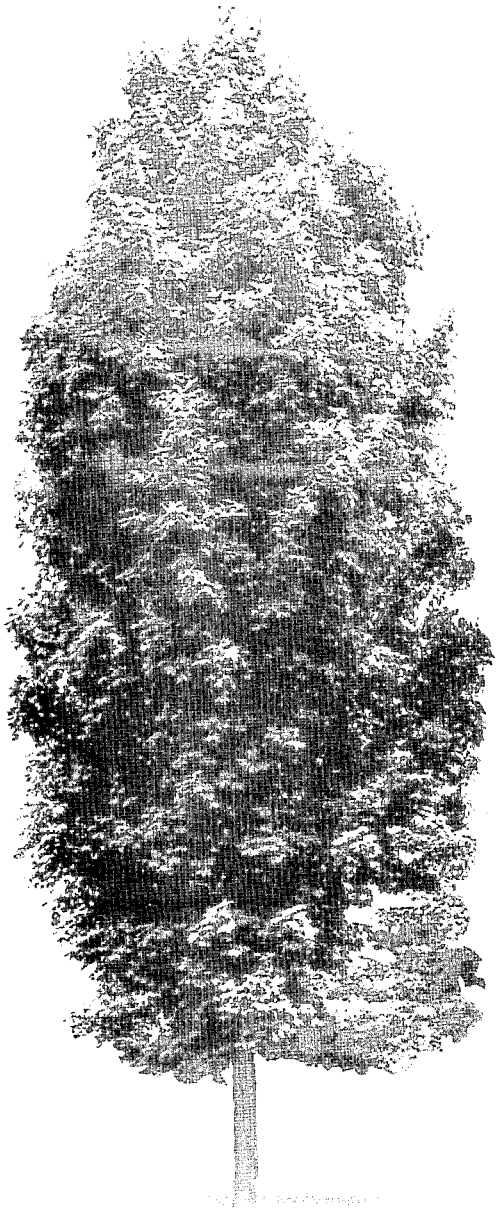
Inventor.
William Flemer, III
By: Robb & Robb
Attorneys.

MAPLE TREE
Filed Dec. 5, 1967
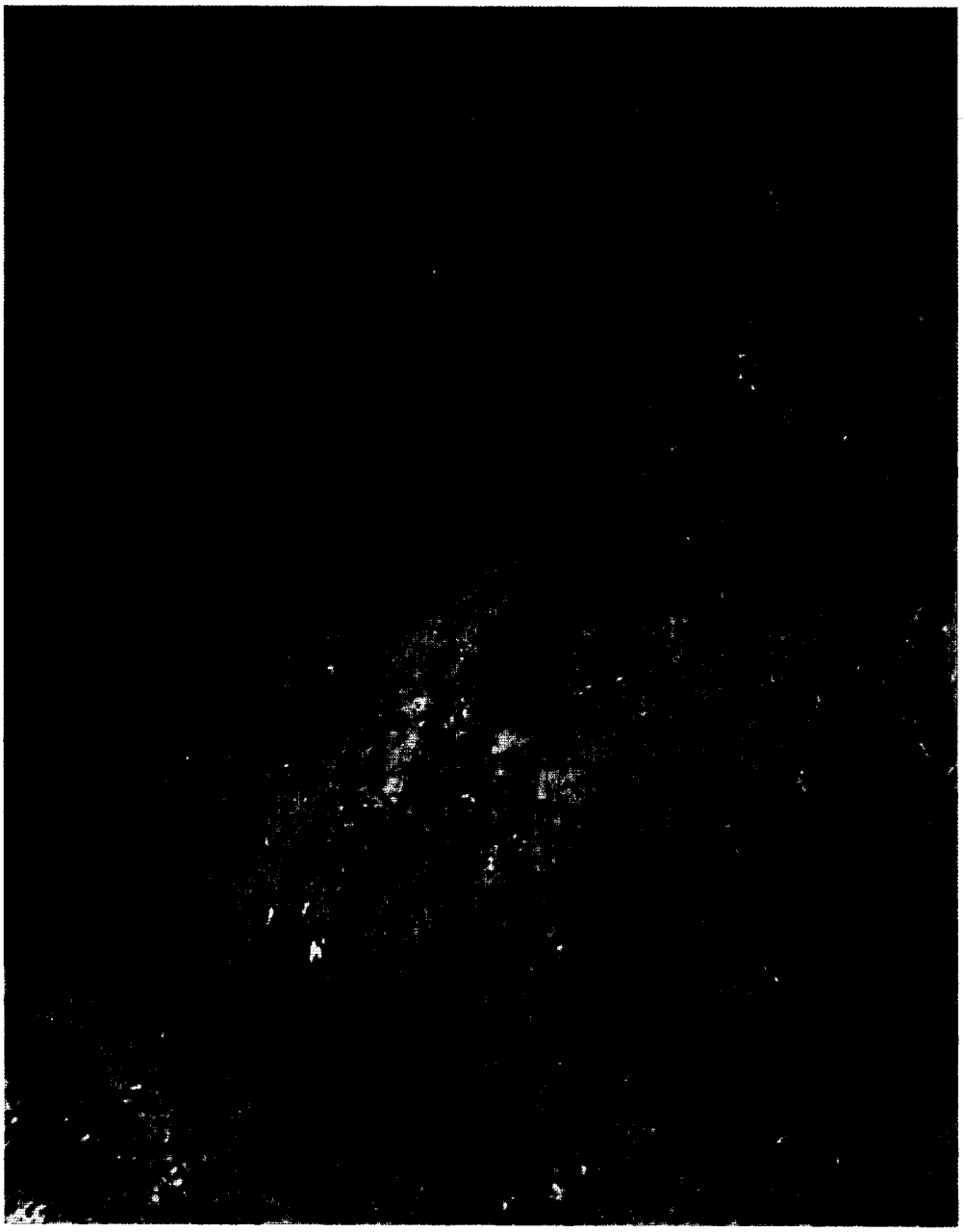
Inventor.
William Flemer, III
By: Robb & Robb
Attorneys.

United States Patent Office

Plant Pat. 2,917
Patented Aug. 12, 1969

2,917
MAPLE TREE

William Flemer III, Princeton, N.J., assignor to Treesearch, Kingston, N.J., a partnership

Filed Dec. 5, 1967, Ser. No. 688,279
Int. Cl. A01h *5/12*
U.S. Cl. Plt.—51 1 Claim

The present invention relates to a new and distinct variety of maple tree of the species botanically known as *Acer saccharum,* which was originated by me by crossing the *Acer saccharum* variety known as "Monumentale" (unpatented) with the *Acer saccharum* variety known as "Columnare" (unpatented), the former being the seed parent and the latter being the pollen parent.

As the result of this breeding, I have produced a new and improved variety of maple tree which is distinguished from its parents, as well as from all other varieties of which I am aware, as evidenced by the following unique combination of characteristics which are outstanding therein:

(1) A more rapid and more full-headed habit of growth than the variety known as "Sentry" (unpatented);

(2) A more dense and compact form than the sugar maple variety known as "Columnare," with even the young trees forming a dense, narrow, rectangular head of foliage;

(3) Leathery, dark green foliage which is resistant to physiological leaf scorch and completely free thereof when other varieties grown adjacent thereto under the same conditions become badly disfigured by such leaf scorch;

(4) The ability to complete its growth early in the season, with consequent freedom from injury from leaf hopper feeding; and (5) A distinctive, attractive and exceptionally brilliant orange fall coloring of the foliage.

Asexual reproduction of my new variety by bud-grafting, as performed by me in Plainsboro Township, N.J., shows that the foregoing characteristics and distinctions come true and are established and transmitted through succeeding propagations.

The accompanying drawings show a typical specimen tree of the new maple variety as depicted in black-and-white to illustrate its general form and habit of growth, and also a portion of a specimen tree depicting the fall color of the foliage.

The following is a detailed description of my new variety, with color terminology in accordance with the Munsell Color Chart, except where general color terms of ordinary dictionary significance are obvious:

Parentage: Seedling.

*Seed parent.*—"Monumentale."
*Pollen parent.*—"Columnare."

Propagation: Holds its distinguishing characteristics through succeeding propagations by bud-grafting.

Locality where grown and observed: Franklin Township, N.J.

Tree: Medium size; upright; narrow and columnar; tall; hardy.

*Trunk.*—Stocky; rough.

*Branches.*—Stocky; smooth. Color—Moderate brown, hue 5YR 3/3. Lenticels—abundant.

Foliage:

*Leaves.*—Abundant, densely borne; about 14 cm. long (not including petiole); about 17 cm. wide; star shaped, with 5 major lobes and 8 minor lobes; very thick. Color—lustrous dark green, hue 2.5G 3/3, changing to strong reddish orange, hue 7.5R 5/13 in the fall. Margin—smooth edge; lobed. Petiole—about 12 cm. long. Glands—none. Stipules—none.

Flower buds: Concealed.

Fruit: A winged samera.

*Borne.*—In October.

*Abundance.*—Sparse.

*Size.*—About 3½ cm. long.

*Color.*—Light brown.

Disease and insect resistance: Entirely free of physiological leaf scorch and leaf hopper infestation, as determined by comparison with other varieties grown under the same conditions and in the same area of New Jersey.

I claim:

1. A new and distinct variety of maple tree, substantially as herein shown and described, characterized particularly as to novelty by the unique combination of a more rapid and more full-headed habit of growth than the variety known as "Sentry" (unpatented), a more dense and compact form than the sugar maple variety known as "Columnare," with even the young trees forming a dense, narrow, rectangular head of foliage, leathery, dark green foliage which is resistant to physiological leaf scorch and completely free thereof when other varieties grown adjacent thereto under the same conditions become badly disfigured by such leaf scorch, the ability to complete its growth early in the season, with consequent freedom from injury from leaf hopper feeding, and a distinctive, attractive and exceptionally brilliant orange fall coloring of the foliage.

No references cited.

ROBERT E. BAGWILL, Primary Examiner